United States Patent [19]

Bille

[11] Patent Number: 4,579,430

[45] Date of Patent: Apr. 1, 1986

[54] METHOD AND APPARATUS FOR FORMING AN IMAGE OF THE OCULAR FUNDUS

[75] Inventor: Josef Bille, Heidelberg, Fed. Rep. of Germany

[73] Assignee: Carl-Zeiss-Stiftung, Heidenheim, Fed. Rep. of Germany

[21] Appl. No.: 559,907

[22] Filed: Dec. 9, 1983

[30] Foreign Application Priority Data

Dec. 11, 1982 [DE] Fed. Rep. of Germany ....... 3245939

[51] Int. Cl.$^4$ .............................................. A61B 3/14
[52] U.S. Cl. .................................................. 351/206
[58] Field of Search ...................... 351/206, 207, 208; 354/62

[56] References Cited

U.S. PATENT DOCUMENTS

4,213,678 7/1980 Pomerantzeff ..................... 351/206

Primary Examiner—Rodney B. Bovernick
Attorney, Agent, or Firm—Walter Ottesen

[57] ABSTRACT

In contrast to techniques currently used such as the fundus camera, the strain to which the patient is exposed during the generation of an image of the ocular fundus is reduced by moving a laser beam across the retina in the form of a scanning raster and by directing the light reflected from the retina through a photoelectric receiver to generate a television image. To achieve a very high resolution, the scanning operation provides at least in the interesting image parts signals which are representative of a greater number of image points than corresponds to the television standard. These image parts are selected sufficiently large to have each point of the raster assigned a separate image signal value when displayed on the television screen. During the time the scanning beam moves within the frame of a selected image part, its intensity is increased for improved image contrast. The apparatus for implementing this image-forming method utilizes at least one polygonal scanner and includes an active image element that cooperates with a sensor to form a closed loop circuit for optical focusing of the image under adaptive control. An electronic shutter is provided to control the intensity of the scanning beam. In addition to the formation of images, the apparatus also permits a measurement to be made of the spatial blood flow distribution in the fundus and of the degree of oxygen saturation of the blood in the retina of the eye under observation.

13 Claims, 7 Drawing Figures

METHOD AND APPARATUS FOR FORMING AN IMAGE OF THE OCULAR FUNDUS

FIELD OF THE INVENTION

The invention relates to a method and an apparatus for forming an image of the ocular fundus.

BACKGROUND OF THE INVENTION

Apparatus to study and photograph the ocular fundus have been on the market for many years under the term fundus camera and have become indispensable aids in ophthalmic diagnostics. They are used, for instance, to study the cardiovascular system using the so-called fluorescein angiography, to diagnose intraocular tumors, to detect vessels damaged by diabetes, to detect detached retinae, etc. In any case, what matters is to obtain an image in which even the finest vessel structures are still discernible.

In the known fundus cameras, the ocular fundus is illuminated by means of a light beam projected on the pupil of the eye, and the light reflected from the eye's retina is directed to an observation microscope for image formation. These devices have meanwhile reached their limits in terms of further improvement possibilities, in particular since the patient's strain-bearing capacity cannot be increased further.

For diagnostic reasons, however, it is desirable to obtain images of the ocular fundus having a still better resolution and improved contrast, while at the same time reducing the strain on the patient as far as possible.

An attempt to progress in this direction is described in U.S. Pat. No. 4,213,678. In the device described in this patent, a collimated laser beam focused through the eye is used for the illumination of a single point on the retina, the beam being deflected in a manner resulting in a sequential point-by-point scanning of the retina in the form of a line-scanning pattern. The light reflected from the retina and passing through the full pupil of the eye is directed to a photoelectric receiver. Its signal output is synchronized with the scanning motion of the laser beam and serves to generate an image on a television monitor.

While in contrast to a fundus camera this known device reduces the strain to which the patient is exposed, it cannot provide a substantial increase in the resolution since the laser beam, due to diffraction, illuminates a relatively large area of the retina (10 μm in diameter, approximately).

This disadvantage cannot be eliminated by improving the external optical imaging system, because the imaging media of the optical apparatus of the eye are invariably affected by optical aberrations. Nor does a magnified representation of a partial area of the retina, to which in this known device the selected scanning field has to correspond, result in a substantial improvement of the achievable resolution. Because of the limited point resolution of the resonant galvanometer scanner used, this known arrangement does not permit the simultaneous generation and representation of both an overview image and an image part of high resolution.

SUMMARY OF THE INVENTION

It is an object of the invention to provide a method and an apparatus for forming an image of the ocular fundus which provides a high-resolution overview image. It is a further object of the invention to provide such a method and apparatus which will also permit the generation of image parts which are freely selectable with regard to their location, afford the same high resolution, have a selectable image contrast and are adapted to be called up and displayed readily and simultaneously with the overview image, without requiring an intervention in the scanning mechanism.

In the method of the invention, an image of the ocular fundus is formed on a television monitor of television means having a predetermined number of image points corresponding to the applicable television standard. The method includes the steps of: scanning a laser light beam across the fundus of the eye in the form of a scanning raster; detecting the light reflected from the fundus with a photoelectric receiver; transmitting the output of the receiver to the television means and forming a television image of the fundus; and, during the scanning of the fundus image field, obtaining signals representative of a number of image points larger than that corresponding to the television standard in at least a part of the fundus, said fundus part being selected to be sufficiently large so as to permit every point of the image raster to be assigned a separate image signal value when displayed on the television screen.

The apparatus for forming an image of the ocular fundus includes: laser means for forming a laser light beam; scanning means for deflecting the light beam in the form of a line scanning raster on the fundus of the eye; receiver means for receiving the reflected scanning raster from the fundus; television means connected to the receiver for receiving the signal output thereof and forming an image of the fundus from the output for viewing by an observer; synchronizing means for synchronizing the raster of the television means to the scanning raster of the scanning means; and, electro-optical means for detecting aberrations of the eye and modulating the same on the laser light beam whereby the image of the fundus formed by the television means is corrected for the aberrations.

With the method and apparatus of the invention, signals representative of a greater number of image points than corresponds to the television standard at least in a partial area are obtained during the scanning of the image field. By designing this partial area sufficiently large, each point of the raster is assigned a separate image signal value when displayed on the television screen. This enables the partial area to be reproduced at the full information density representable in the television image.

It is possible to operate in the online mode and to select the image part by means of a so-called light pen, for example. For this purpose, it is possible for instance to have initially an overview image produced in a first scanning operation and to select the part to be emphasized on the basis of this overview image. In a subsequent second scanning operation, the scanning of this selected part yields signals representative of a greater number of image points than corresponds to the television standard.

It is also possible to obtain during the scanning of the entire image field signals representative of a greater number of image points than corresponds to the television standard. These signals are suitably digitalized and stored in memory. In the actual evaluation operation, the stored signals are represented as an overview image from which an image part is selectable. Since the number of image point signals available for this image part in the storage medium is equal to the number representable in the television image, it is possible to display a magnified image part of the same high resolution as the overview image without the need for another scanning operation.

In both modes of operation, no intervention in the deflection mechanism occurs. The image point signals are available in sufficient numbers for the selected image part to contain all representable information items. Accordingly, this image part is enlarged out of the overview image by means of an electronic magnifying glass, the resolution in the image part being improved in accordance with the selected coefficient of magnification.

Irrespective of the mode of operation chosen, it is particularly advantageous after selection of the image part to increase the intensity of the scanning laser beam within the frame delimiting the image part. This results in an improvement of the image contrast in the image part without appreciably increasing the overall light exposure of the patient's eye. Accordingly, the image part is viewed by means of what may be referred to as an intensity magnifying glass.

It will be apparent from the foregoing that this new method enables a selected part of the ocular fundus to be viewed with improved resolution and higher image contrast, whereby the strain to which the patient is exposed is even less than would be the case with a conventional fundus camera.

The method of this invention permits particularly the display of the overview image and of the selected image part on separate monitors simultaneously, thus clearly indicating to the viewer the accurate position of the image part in the field at all times.

The apparatus to implement the method of this invention is to be designed in a manner permitting during the scanning of the image field the obtainment of signals representative of a greater number of image points than are representable in a television image. When applying the C.C.I.R. television standard, for example, this means that significantly more than 800 image points have to be resolved in each scan line. In conventional eye observation, the aim is to obtain a usable deflection angle of 30° at which the field of view on the retina covers an area of about 8 mm in diameter. It is obvious that with the apparatus known from U.S. Pat. No. 4,213,678 the required high resolution is in principle not attainable because the errors caused by the aberrations of the optical imaging system of the eye do not allow the laser beam to be brought to a spot diameter on the retina of less than 10 $\mu$m, approximately.

The apparatus of this invention remedies this situation by providing a polygonal scanner for fast and linear scanning of the image field in at least one direction of the coordinates, and by disposing an active image element between the laser light source and the scanners, the image element cooperating with a sensor to form a closed loop circuit for optical focusing of the image under adaptive control.

The active image element is advantageously designed as an active mirror as known per se from literature describing other uses. The sensor in the control loop is suitably a wave-front sensor. A control loop essentially comprised of these elements permits the image to be focused under adaptive control, i.e., it enables image deteriorations caused by the aberrations of the optical imaging system and the transmitting media of the eye to be compensated for.

In the apparatus of this invention, the illuminating laser beam is generally widened to a diameter of between 3 mm and 4 mm, in exceptional cases even still wider, and by compensating for all existing aberrations, it is possible to focus the laser beam on a spot of a minimal diameter of between 2 $\mu$m and 3 $\mu$m on the retina. This permits the resolution of more than 5,000 image points per scan line, that is, it is possible for example to resolve and represent individual receptors in the fovea.

Since the use of optical image focusing under adaptive control produces data on the wave front of the imaging laser beam, the apparatus of this invention enables the refractive index profile within the eye to be reconstructed, permitting for the first time an automatic determination of the refraction at high accuracy.

In the new apparatus, the deflection of the illuminating laser beam in at least one direction of the coordinates is performed by means of a polygonal scanner, the light beam being deflected by means of a rapidly rotating polygonal mirror. The polygonal mirror is suitably used for scanning in direction x, i.e., in the direction of the television lines. For scanning in direction y, a polygonal scanner may likewise be used, however it is also possible to achieve the deflection using a galvanometer mirror.

In either case, it is necessary to obtain from the laser-beam deflecting elements synchronizing pulses which serve to synchronize the raster of the television monitor used for image generation with the scanning raster.

By the utilization of simple means, the apparatus for forming an image of the ocular fundus constructed in accordance with this invention may have its function extended by being employed as an apparatus for measuring the blood flow and the oxygen saturation of the blood. Such measurements are very valuable to the examining physician since the diagnosis arrived at on the basis of the image of the ocular fundus can be corroborated by such measurements without the need to apply another device.

The blood flow is measured by means of a laser Doppler velocimeter the construction of which will become apparent from the subsequent description of the figures. This device permits determination of the spatial blood flow distribution in the ocular fundus which is of particular importance for diabetes examinations.

The measurement of the oxygen saturation of the blood is a measure of the spatial distribution of oxygen saturation in the retina which is of importance for diabetes and cardiovascular system examinations.

Devices for measuring blood flow and oxygen saturation of the blood are known per se. The present invention provides a novel and particularly valuable possibility to perform these measurements with the same device that serves for the formation of a high-resolution and high-contrast image of the ocular fundus.

BRIEF DESCRIPTION OF THE DRAWING

The invention will now be described with reference to the drawing wherein.

DESCRIPTION OF THE PREFERRED EMBODIMENTS OF THE INVENTION

Figure 1:
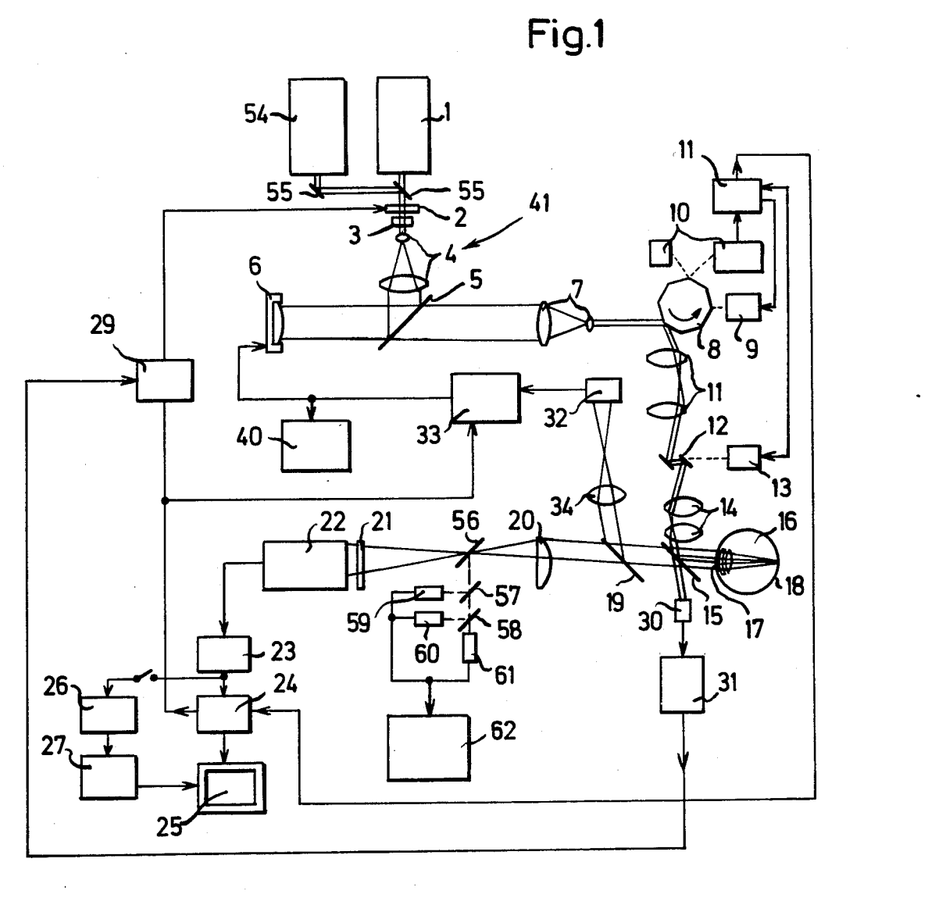
FIG. 1 is an embodiment of the apparatus of the invention for forming an image of the ocular fundus.

Referring now to FIG. 1, reference numeral 1 identifies a laser utilized as a light source which can, for example, be configured as a 2 mW helium-neon laser which emits light at a wavelength of 633 nm. The light emitted by the laser passes through an electrically controllable shutter 2 which can, for example, be a Pockels cell and a polarization filter 3. The laser beam is widened by optical system 4 illustrated schematically and is directed to an active mirror 6 via a semi-transparent mirror 5. The light reflected from this mirror 6 passes through an optical system 7 and impinges upon a polygonal mirror 8 which is rotated by means of a motor 9 in the direction of the arrow.

If the polygonal mirror 8 is for example made up of twenty facets, then its rotational speed is approximately 12,000 revolutions per minute. During its rotation, the mirror 8 deflects the laser beam linearly in line direction x. At a line repetition rate of 4 KHz, a useable deflection angle of 30° is obtained with a 20% dead time caused by the change of facets. System 10 shown schematically generates synchronizing pulses which identify the beginning and end of each scan line. These pulses are directed to a control unit 11.

Such a polygonal scanner is disclosed, for example, in the journal entitled "Analytical and Quantitative Cytology", Vol. 3, No. 1, March 1981, pages 55 to 66, especially pages 57 and 63.

The optical deflecting plane is imaged upon a linear galvanometer scanner 12 via an objective 70. The galvanometer scanner 12 deflects the laser beam in the vertical direction in a saw-tooth form. An arrangement 13 is provided which drives the scanner 12 and which is supplied with control pulses via the control unit 11. The control unit 11 couples all control signals to the mirror reference signal of the system 10 in a phase-stable manner. This is necessary because the high inertia of the rotating polygonal mirror 8 does not permit the rotational speed of the latter to be controlled to a definite cycle.

The illuminating laser beam is imaged on the pupil of the eye 16 via a further objective 14, with the beam being transmitted into the eye via a semi-transparent mirror 15. The illuminating beam has a reduced diameter in the pupillary plane 17 of the eye 16 since the pupillary plane 17 is conjugated to the deflection planes of the scanners 8 and 12.

The rays reflected on the retina 18 pass through a semi-transparent mirror 19 and are then collected by a non-spherical lens 20 having a high aperture ratio. Thereafter, the rays pass through a further polarization filter 21 and are detected by means of a receiver 22 in the region of a plane conjugated to the pupillary plane 17 of the eye 16.

The signals delivered by the receiver 22 are amplified in amplifier 23 and are fed to a television monitor 25 via a standard television signal generator 24. The standard television signal generator 24 is controlled by control unit 11 and delivers the synchronizing pulses necessary for generating the image. In this way, an image of the ocular fundus 18 becomes visible on the monitor 25 since the scanning raster described by the illuminating laser beam on the retina 18 corresponds to the television raster.

If desired, the signals coming from the receiver 22 can also be digitalized in the converter 26 after they are amplified in amplifier 23 and then stored in a memory 27. This memory 27 can be configured as a refresh memory of a digital image system which, after the end of the read-in cycle, illustrates the image signals on the monitor 25 in such a manner that they are phantom color coded. It is also possible to configure the memory 27 as a long-term storage memory. In this instance, the image signals are always recallable so that, for example, a comparison of images generated at different points in time is possible. Also, a measured evaluation of the image signals can thereby be made at any time.

Figure 2:
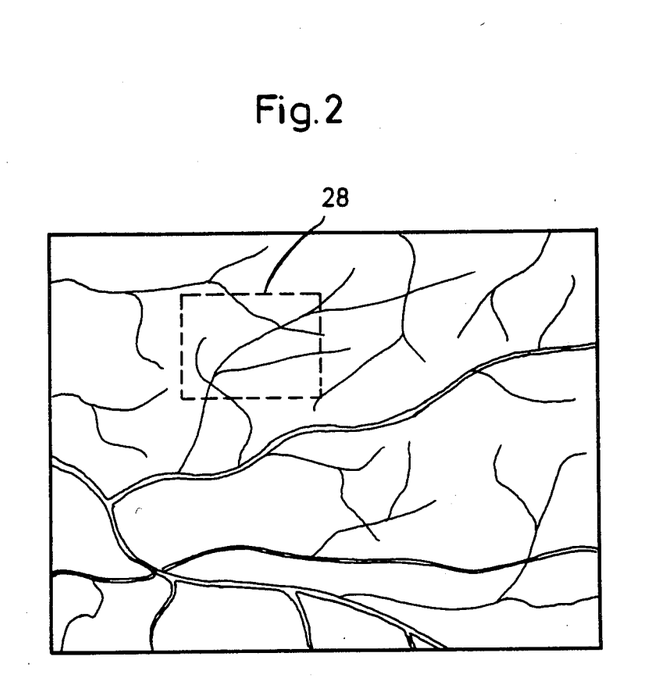
FIG. 2 is an exemplary image of the ocular fundus generated by the apparatus according to FIG. 1.

The polarizers 3 and 21 are arranged in a crossed relationship to each other. In this way, the corneal reflex is suppressed. In cooperation with the electronic shutter 2, a definite part of the fundus selected from the overview image on the monitor 25 can be emphasized by increasing its intensity. FIG. 2 serves to provide a more detailed explanation, showing an overview image which, for example, is generated by scanning the retina 18 of the eye 16 by means of the scanners 8 and 12. With the aid of a light pen, a part 28 of the fundus, for example, can be selected from the overall image on the monitor 25 in a known manner. The generator 24 then generates the necessary synchronizing pulses which cause a higher intensity of the laser image to be passed through the shutter 2 via the switching arrangement 29 as long as the scanning beam moves within the selected part 28. This intensity is therefore higher than the intensity associated with a movement of the scanning beam outside of the part 28. This part 28 thereby appears emphasized by means of a so-called intensity magnifying glass and has a better image contrast than the surrounding field. The part 28 is suitably reproduced in lieu of the overview image and fills out the format of the monitor 25. Of course, it is also possible to utilize two monitors so that both the overview image and the image of the part 28 can be simultaneously reproduced and illustrated.

With this arrangement, it is possible to definitively locate damaged vessels by means of the overview image or by means of the image of the selected part. The electronic shutter 2 functions so rapidly that it is also possible to photocoagulate the damaged vessels by means of a momentary increase in the intensity of the laser light. In this method, it is assured that the light intensity is only then increased when the scanning beam has reached the coordinates of the vessels to be coagulated.

As shown in FIG. 1, the illuminating laser beam impinges upon a receiver 30 via the mirror 15 arranged in front of the eye 16. The receiver 30 serves to control the applied power and automatically switches the laser beam off via control unit 31 and the shutter 2 as soon as this power reaches impermissibly high values. At the same time, this receiver 30 serves to eliminate variations in intensity of the illuminating laser beam by means of regulation via the shutter.

It has been shown that the images obtained by scanning and illustrated on the monitor 25 have a more plastic appearance than do the images obtained with a fundus camera of conventional construction. In order to be able to select the optimal plasticity, it is desirable to utilize a variable-frequency dye laser in lieu of the helium-neon laser 1. This makes it possible to select the most suitable wavelength of the illuminating projector.

An active image element 6 is arranged in the illuminating beam path of the apparatus of FIG. 1 and serves to optically improve the image by adaptive control within a closed loop circuit. This control circuitry includes a schematically-illustrated wave-front sensor 32 which detects the optical aberrations of the image of the retina 18 which is deflected upon the sensor by the mirror 19. The aberrations are controlled via a control circuit and the image element 6 to be described below.

Figure 3:
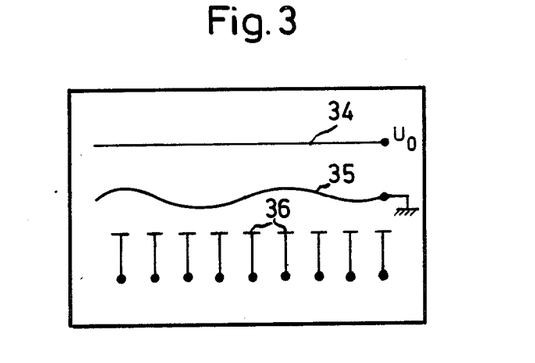
FIG. 3 is a schematic of the active mirror utilized in the apparatus of FIG. 1.

In the illustrated embodiment, a membrane mirror is selected as the active image element 6 and is known from the Journal of the Optical Society of America, vol. 67 (1977), No. 3, March 1977, pages 399 to 406. As the schematic illustration of FIG. 3 shows, such a mirror comprises a transparent electrode 34 which is evaporated on a glass window and has a voltage $U_o$ applied to it. A grounded mirror foil 35 is arranged at a short distance (approximately 50 $\mu$m) from this electrode. The mirror foil 35 is a thin plastic foil approximately 0.5 $\mu$m thick and vapor-coated with aluminum. At short spacing of approximately 50 $\mu$m from the other side of the foil 35, an array of several electrodes 36 is arranged which are individually controllable. The control of the electrodes 36 is effected with a voltage $U_o \pm U_i$ which develops a resulting electrostatic force that acts on the foil 35. In this way, the mirror 6 corresponds to a multichannel electrometer, with the maximum deflection of the foil 35 lying in the area of magnitude of 1 $\mu$m.

Figure 4:
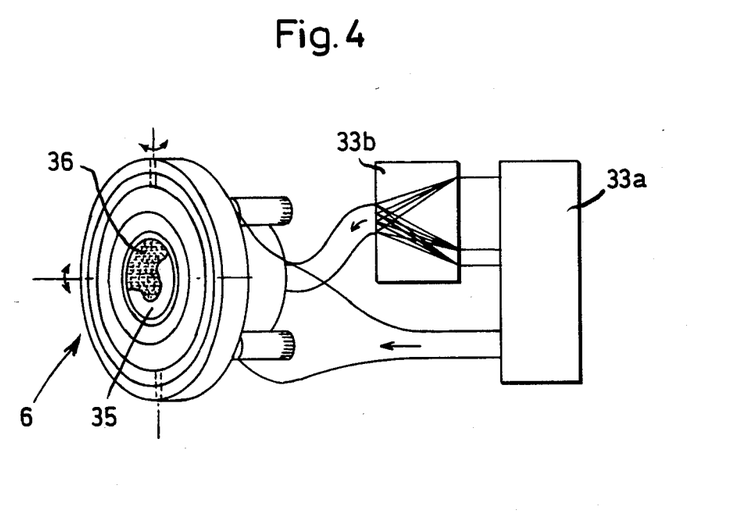
FIG. 4 is a perspective view of the active mirror.

The control of mirror 6 is suitably effected on the basis of a modal control process. For this purpose, basic forms of optical aberration such as an astigmatism, spherical aberration, defocusing and coma are modulated upon the illuminating laser beam in a plane conjugated to the pupillary plane 17 of the eye 16. As shown in FIG. 4, this is effected by means of a control unit 33. The control unit 33 includes an arrangement 33a which generates the signals corresponding to the above-mentioned selected basic forms of optical aberration. The control unit 33 includes a further arrangement 33b for distributing the signals to the electrodes 36.

Figure 5:
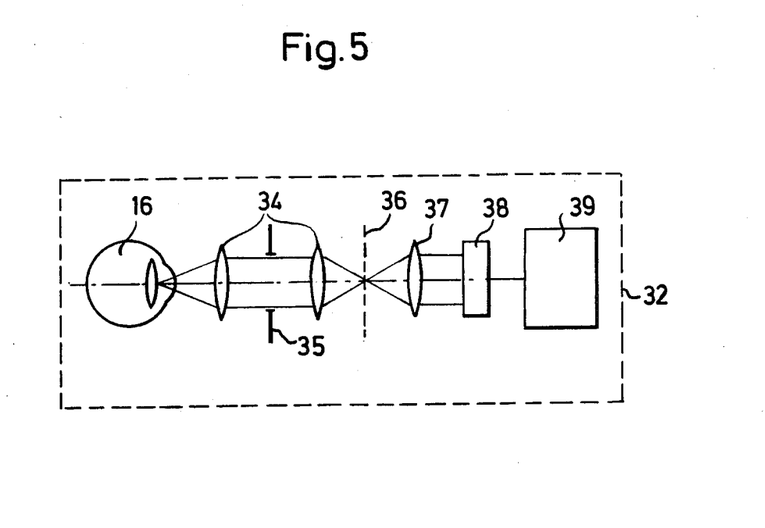
FIG. 5 is a separate schematic showing the configuration of the wave-front sensor utilized in the apparatus of FIG. 1.

The image generated after switching in the mirror 6 is cast upon a wave-front sensor 32 via the mirror 19. An example of the configuration of this wave-front sensor 32 is shown in FIG. 5.

The light reflected from the eye 16 is imaged on a rotating matrix 36 by means of an optical system 34. The optical system 34 includes a conjugated aperture plane at the location indicated by reference numeral 35. The interference pattern generated thereby is imaged on a diode array 38 via the optical system 37. The diode array 38 measures the profile of the wave-front. From this, signals are obtained via the processor 39 which adjust the active mirror 6 via the arrangement 33 until the optimal focusing parameters are determined which compensate for all optical aberrations of the eye 16 to be examined.

When the optimal corrective condition is reached, the illuminating laser beam, which is widened to a diameter of approximately 4 mm, can be focused to a minimal focal magnitude of approximately 2.5 $\mu$m in diameter on the retina 18.

The data on the wave front of the imaging laser beam, which is obtained with the above-described optical focusing of the image under adaptive control, makes it possible to reconstruct the refraction profile within the eye 16. The arrangement 40 is provided for this purpose. The arrangement 40 is so configured that it shows the data obtained and/or prints the same.

The corrective data determined for the mirror 6 is stored in the memory of the control unit 33 and is always recallable therefrom in real time.

Before the eye 16 is observed by the physician, the aberrations are first determined by the above-described optical focusing of the image under adaptive control. For this purpose, a separate investigation is performed. In this procedure, the optimal focusing parameters are determined at a data rate of, for example, 100 lines per second in various directions. The aberration data thereby determined for the eye 16 is stored in the data memory of the computer 33. It is, for example, possible during an image-forming time of 80 milliseconds to obtain a resolution of 800 subapertures using 63 corrective electrodes 36 within a selected fundus section. This is made possible because of the speed of the active mirror 6 and the data processing.

During the actual investigative procedure, the corrective values for the mirror 6 are recalled in real time from the memory of the computer 33 so that geometric true scale fundus images can be generated which are not falsified by the optical aberrations of the eye.

By scanning the retina 18 by means of an illuminating laser beam corrected via the mirror 6, signals are obtained in a scan line which are representative of a greater number of image points than can be shown on the television screen of the monitor 25. In this way, more than 5000 image points can be resolved in a line. The monitor 25 therefore shows an overview image of signals which are averaged.

If, for example, part 28 of FIG. 2 is selected from the overview image for a more precise examination, this part fills out the format of the monitor 25 so that it takes up the whole screen whereby the full resolution is reached if the part 28 is selected to reflect an appropriate magnitude. The standard signal generator 24 provides for such an adaptation.

With the apparatus of FIG. 1, it is thus possible to observe an image section with improved image resolution without requiring any kind of adjustment to the optical system of the apparatus. Accordingly, one can characterize the foregoing as obtaining an image enlargement by means of an electronic magnifying glass.

It is possible and advantageous to also make use of the intensity magnifier at the same time; that is, the selected image part can be scanned with greater intensity. In this way, a detailed illustration of the fundus image with a high resolution and high image contrast is made possible for the first time. The resolution is so large that individual receptors in the fovea are resolved.

It is generally not necessary to correct the illuminating laser beam optimally over the entire image field by means of the active mirror 6. Of special interest are mostly small image fields, for example, the fovea or also individual vessels.

For this reason, an overview image is generally generated first, and the mirror 6 remains inactive. On the basis of this overview image, the interesting parts are then selected on the monitor 25 and the optical focusing of the image under adaptive control is carried out with respect to these parts. The corrective values determined thereby are stored in the computer 33.

In the subsequent enlarged illustration of the selected parts, the parts are illustrated on the monitor 25 with a high image sharpness and high contrast.

When investigating the abnormal eye, for example the eye which is extremely myopic or also after a cataract operation, it may also be suitable to correct the illuminating beam over the entire image field in order to obtain a good overview image on the one hand and, on the other hand, to permit the selection of any desired part.

In order to obtain a high resolution of the image with the apparatus of FIG. 1 also in the vertical direction, it is possible to employ an image window which is in a form of stripes and contains all image lines to be realized by means of the scanner 12. This image window is then displaced in the vertical direction and the entire image is put together from the individual stripes in the memory 27.

The apparatus according to the invention is especially advantageously configured so that in addition to providing high-precision image illustration, it can also measure the spatial blood flow distribution in the fundus as well as the spatial distribution of the oxygen saturation of the blood in the retina.

Figure 6:
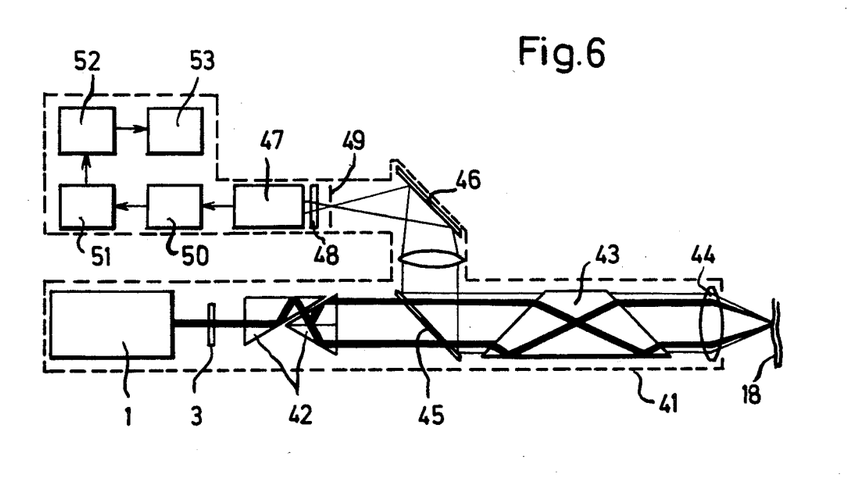
FIG. 6 is an embodiment of a laser Doppler velocimeter for measuring the flow of blood; and, FIG. 7 is a graph showing the dependence of the extinction coefficient of hemoglobin and oxyhemoglobin on wave length.

A differential laser Doppler velocimeter 41 is utilized for measuring the spatial blood flow distribution and is illustrated separately in FIG. 6. The beam of the helium neon laser 1 is divided into two parallel beams of the same intensity by the prism system 42. The beams pass through the dove prism 43 and the objective 44 and are imaged on a common point of the retina 18. An interference pattern occurs in the region where the volume is measured. Erythrocytes which transverse this light matrix generate a scatter signal having a modulation frequency which is proportional to the stripe distance and to the particle velocity. This scatter signal is directed via mirrors 45, 46 to a receiver 47 in front of which an interference filter 48 and an aperture 49 are arranged. The measuring signal delivered by the receiver 47 is filtered by a band-pass filter 50, is digitalized in a converter 51 and temporarily stored in a microprocessor system 52. The capacity spectrum is there computed with the aid of a time-optimized Fast Fourier transformation from which the speed of flow is determined and indicated at 53.

The velocimeter of FIG. 6 is not shown in FIG. 1 in order to avoid complicating the schematic. Its location in FIG. 1 is indicated by arrow 41, that is, it practically replaces the optical system 4. The lens 44 in FIG. 6 is defined by the lens of the eye 16.

The apparatus of FIG. 1 can also be operated with a helium-selenium laser 54 having a beam which is mirrored in via mirror 55. Such a laser can, for example, have an output power of 100 milliwatts and extend over a great many lines in the visible region of the spectrum. The yellow laser lines in the region of the absorption of the hemoglobin and oxyhemoglobin molecule are suitable for measuring the degree of oxygen saturation in the blood vessels of the retina. Because of the different spectral absorption characteristics of the oxyhemoglobin and of the deoxygenated hemoglobin, the degree of oxygen saturation can be determined by measuring at the wavelengths of 559 nm, 569 nm, and 586 nm. For this purpose, the light reflected from the eye 16 is directed via a mirror 56 and two spectral mirrors 57 and 58 to three receivers 59, 60 and 61. The spectral signals generated by these units are transmitted to a computer 62 computing the oxygen saturation.

Figure 7:
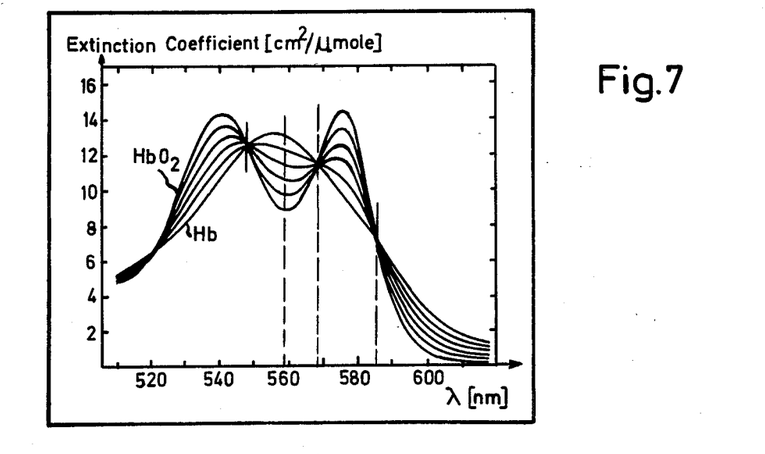

FIG. 7 shows the wavelength dependence of the extinction coefficients of hemoglobin and oxyhemoglobin. The measurement is made at a wavelength of 559 nm, whereas at the wavelengths of 569 nm and 586 nm isobesto points exist which are used to form a standard. In order to compensate for the normally present scatter, it can be advantageous to utilize two or three further wavelengths generated by the laser 54. In this way, the signal-to-noise ratio can be improved.

It is understood that the foregoing description is that of the preferred embodiments of the invention and that various changes and modifications may be made thereto without departing from the spirit and scope of the invention as defined in the appended claims.

What is claimed is:

1. A method for forming an image of the ocular fundus on a television monitor of television means having a predetermined number of image points corresponding to the applicable television standard, the method comprising the steps of:
    scanning a laser light beam across the fundus of the eye in the form of a scanning raster;
    detecting the light reflected from the fundus with a photoelectric receiver;
    transmitting the output of said receiver to said television means and forming a television image of the fundus; and,
    during the scanning of the fundus image field, obtaining signals representative of a number of image points larger than that corresponding to said television standard in at least a part of the fundus, said fundus part being selected to be sufficiently large so as to permit every point of the image raster to be assigned a separate image signal value when displayed on the television screen.

2. The method of claim 1 wherein, during the scanning of the entire fundus image field, signals are obtained representative of a number of image points larger than that corresponding to said television standard.

3. The method of claim 1, said step of scanning a laser light beam across the fundus of the eye being a first scanning step to obtain an overview image; and, the method comprising: the further steps of selecting a part of the overview image; and, conducting a second scan wherein the image part is scanned and signals representative of a number of image points larger than that corresponding to said television standard are obtained.

4. The method of claim 3 comprising: the further step of increasing the intensity of the illuminating laser beam during said second scan.

5. The method of claim 4 comprising: the further step of displaying the overview image simultaneously with said image part.

6. An apparatus for forming an image of the ocular fundus comprising:
    laser means for forming a laser light beam;
    scanning means for deflecting said light beam in the form of a line scanning raster on the fundus of the eye;
    receiver means for receiving the reflected scanning raster from the fundus;
    television means connected to said receiver for receiving the signal output thereof and forming an image of the fundus from said output for viewing by an observer;
    synchronizing means for synchronizing the raster of said television means to the scanning raster of said scanning means; and,
    electro-optical means for detecting aberrations of the eye and modulating the same on said laser light beam whereby said image of the fundus formed by said television means is corrected for said aberrations.

7. An apparatus for forming an image of the ocular fundus comprising:

laser means for forming a laser light beam;

scanning means for directing said light beam onto the fundus of the eye, said scanning means including a polygonal scanner for deflecting and rapidly scanning said light beam linearly across the fundus in at least one coordinate direction;

receiver means for receiving the scanning raster reflected from the fundus;

television means connected to said receiver for receiving the signal output thereof and forming an image of the fundus from said output for viewing by an observer;

synchronizing means for synchronizing the raster of said television means to the scanning raster of said scanning means; and, closed-loop electro-optical control circuit means for adaptive-optically improving said image formed by said television means, said control circuit means including:

sensor means for detecting the optical aberrations of the fundus image and for generating electrical signals indicative of said aberrations; and, active image means for receiving said electrical signals and being interposed in the path of said light beam for modulating said aberrations onto said light beam whereby said image of the fundus formed by said television means is corrected for said aberrations.

8. The apparatus of claim 7, said active image means being an active mirror.

9. The apparatus of claim 7, said sensor means being a wave-front sensor.

10. The apparatus of claim 7 comprising: polarization means for polarizing the light of the light beam so as to suppress the corneal reflex of the eye under observation, said polarization means including: a first polarizer arranged directly behind said laser means when viewed in the direction of the light beam; and a second polarizer arranged in the path of the light reflected from the fundus and disposed in front of said receiver means, said first and second polarizers being in a crossed relationship to each other; and, the apparatus further comprising: electronic shutter means arranged between said laser means and said first polarizer, said television means including generator means connected to said shutter means for adjusting the latter.

11. The apparatus of claim 7, said television means including memory means for storing the image of a fundus.

12. The apparatus of claim 7 comprising means for measuring the spatial blood flow distribution in the fundus.

13. The apparatus of claim 7 comprising means for measuring the spatial distribution of oxygen saturation of the blood in the retina of the eye under observation.

* * * * *